US006371732B1

(12) United States Patent
Moubayed et al.

(10) Patent No.: US 6,371,732 B1
(45) Date of Patent: Apr. 16, 2002

(54) CURVILINEAR PERISTALTIC PUMP

(76) Inventors: Ahmad Maher Moubayed, 28245 San Marcos, Mission Viejo, CA (US) 92692; Oscar E. Hyman, 16019 Virginia Point Rd., Poulsbo, WA (US) 98370; Robert L. Jones, 6650 Canyon Hills Rd., Anaheim, CA (US) 92807; David Norman White, 31061 Via Limon, San Juan Capistrano, CA (US) 92675

( * ) Notice: Subject to any disclaimer, the term of this patent is extended or adjusted under 35 U.S.C. 154(b) by 0 days.

(21) Appl. No.: 09/639,970

(22) Filed: Aug. 16, 2000

Related U.S. Application Data

(63) Continuation of application No. 09/189,052, filed on Nov. 9, 1998, now Pat. No. 6,164,921.

(51) Int. Cl.[7] .......................... F04B 49/06; F04B 43/08
(52) U.S. Cl. ...................................... 417/44.1; 417/474
(58) Field of Search ............................... 417/44.1, 474, 417/477.3, 477.9, 477.11; 251/7

(56) References Cited

U.S. PATENT DOCUMENTS

| 762,620 A | 6/1904 | Eastwood |
| 3,011,684 A | 12/1961 | Corneil |
| 3,115,152 A | 12/1963 | Goldberg |
| RE26,006 E | 4/1966 | Gewecke |
| 4,025,241 A | 5/1977 | Clemens |
| 4,199,307 A | 4/1980 | Jassawalla |
| 4,493,706 A | * 1/1985 | Borsanyi et al. ............ 604/153 |
| 4,585,439 A | 4/1986 | Michel |
| 4,657,486 A | 4/1987 | Stempfle et al. |
| 4,671,792 A | 6/1987 | Borsanyi |
| 4,696,671 A | 9/1987 | Epstein et al. |
| 4,869,646 A | 9/1989 | Gordon et al. |
| 4,946,448 A | 8/1990 | Richmond |

(List continued on next page.)

FOREIGN PATENT DOCUMENTS

| EP | 0510881 A | * 10/1992 |
| FR | 1.529.535 | 6/1968 |
| GB | 1025947 | * 4/1966 |
| JP | 2-125983 | 5/1990 |
| WO | WO9734084 | 9/1997 |
| WO | WO 97/34084 | 9/1997 |

*Primary Examiner*—Charles G. Freay
*Assistant Examiner*—Michael K. Gray
(74) *Attorney, Agent, or Firm*—Stetina Brunda Garred & Brucker

(57) ABSTRACT

A curvilinear peristaltic pump for facilitating the pumping of a liquid through a length of resilient tubing. The pump comprises a housing having a platen member attached thereto and a rotatable cam disposed therewithin. Also disposed within the housing is a drive unit of the pump which is mechanically coupled to the cam such that the activation of the drive unit results in the concurrent rotation of the cam in a first direction and the deactivation of the drive unit maintains the cam in a set position. Movably attached to the housing are a plurality of pump fingers of the pump, each of which has a first end which is cooperatively engaged to the cam and a second end which is disposed in spaced relation to the platen member. The cam is configured to sequentially move the pump fingers radially outwardly toward and inwardly away from the platen member when rotated in the first direction by the drive unit. A portion of the tubing may be extended between the platen member and the second ends of the pump fingers such that the sequential movement of the pump fingers toward and away from the platen member results in liquid within the tubing being pumped in the first direction of rotation of the cam. The pump is used in conjunction with a disposable tubing assembly which is provided with a shut-off valve to selectively obstruct the flow of liquid through the tubing assembly.

3 Claims, 6 Drawing Sheets

Microfiche Appendix Included
(3 Microfiche, 189 Pages)

U.S. PATENT DOCUMENTS

| | | | |
|---|---|---|---|
| 4,969,874 A | 11/1990 | Michel et al. | |
| D322,124 S | 12/1991 | Lichte et al. | |
| 5,078,683 A | * 1/1992 | Sancoff et al. | 417/474 |
| 5,087,250 A | 2/1992 | Lichte et al. | |
| 5,090,877 A | 2/1992 | D'Silva | |
| 5,100,380 A | 3/1992 | Epstein et al. | |
| 5,108,367 A | 4/1992 | Epstein et al. | |
| D326,152 S | 5/1992 | Rutter | |
| D326,329 S | 5/1992 | Ballstadt | |
| 5,135,500 A | 8/1992 | Zdeb | |
| 5,153,827 A | 10/1992 | Coutré et al. | |
| 5,158,533 A | 10/1992 | Strauss et al. | |
| 5,176,644 A | 1/1993 | Srisathapat et al. | |
| 5,192,269 A | 3/1993 | Poli et al. | |
| 5,244,461 A | 9/1993 | Derlien | |
| 5,254,083 A | * 10/1993 | Gentelia et al. | 604/35 |
| 5,279,550 A | 1/1994 | Habib et al. | |
| 5,303,093 A | 4/1994 | Kawasaki | |
| 5,304,126 A | 4/1994 | Epstein et al. | |
| 5,306,257 A | 4/1994 | Zdeb | |
| 5,317,506 A | 5/1994 | Coutré et al. | |
| 5,322,422 A | * 6/1994 | Natwick et al. | 417/474 |
| 5,378,231 A | 1/1995 | Johnson et al. | |
| 5,389,078 A | 2/1995 | Zalesky et al. | |
| 5,431,627 A | 7/1995 | Pastrone et al. | |
| 5,433,710 A | 7/1995 | VanAntwerp et al. | |
| 5,437,635 A | 8/1995 | Fields et al. | |
| 5,445,621 A | 8/1995 | Poli et al. | |
| 5,462,256 A | 10/1995 | Minick et al. | |
| 5,462,525 A | 10/1995 | Srisathapat et al. | |
| 5,464,392 A | 11/1995 | Epstein et al. | |
| 5,485,408 A | 1/1996 | Blomquist | |
| 5,496,273 A | 3/1996 | Pastrone et al. | |
| 5,514,103 A | 5/1996 | Srisathapat et al. | |
| 5,526,853 A | 6/1996 | McPhee et al. | |
| 5,531,680 A | 7/1996 | Dumas et al. | |
| 5,531,698 A | 7/1996 | Olsen | |
| 5,540,561 A | 7/1996 | Johnson | |
| 5,547,470 A | 8/1996 | Johnson et al. | |
| 5,554,013 A | 9/1996 | Owens et al. | |
| 5,564,915 A | 10/1996 | Johnson | |
| 5,567,136 A | 10/1996 | Johnson | |
| 5,569,186 A | 10/1996 | Lord et al. | |
| 5,575,631 A | * 11/1996 | Jester | 417/474 |
| D376,848 S | 12/1996 | Zeilig et al. | |
| 5,620,312 A | 4/1997 | Hyman et al. | |
| 5,628,619 A | 5/1997 | Wilson | |
| 5,630,710 A | 5/1997 | Tune et al. | |
| D380,260 S | 6/1997 | Hyman | |
| 5,637,093 A | 6/1997 | Hyman et al. | |
| 5,637,095 A | 6/1997 | Nason et al. | |
| 5,647,853 A | 7/1997 | Feldmann et al. | |
| 5,647,854 A | 7/1997 | Olsen et al. | |
| 5,658,133 A | 8/1997 | Anderson et al. | |
| 5,660,529 A | 8/1997 | Hill | |
| 5,665,065 A | 9/1997 | Colman et al. | |
| 5,683,233 A | 11/1997 | Moubayed et al. | |
| 5,683,367 A | 11/1997 | Jordan et al. | |
| 5,695,473 A | 12/1997 | Olsen | |
| 5,700,245 A | 12/1997 | Sancoff et al. | |
| 5,712,795 A | 1/1998 | Layman et al. | |
| 5,718,569 A | 2/1998 | Holst | |
| 5,842,841 A | 12/1998 | Danby et al. | |
| 5,879,144 A | 3/1999 | Johnson | |

* cited by examiner

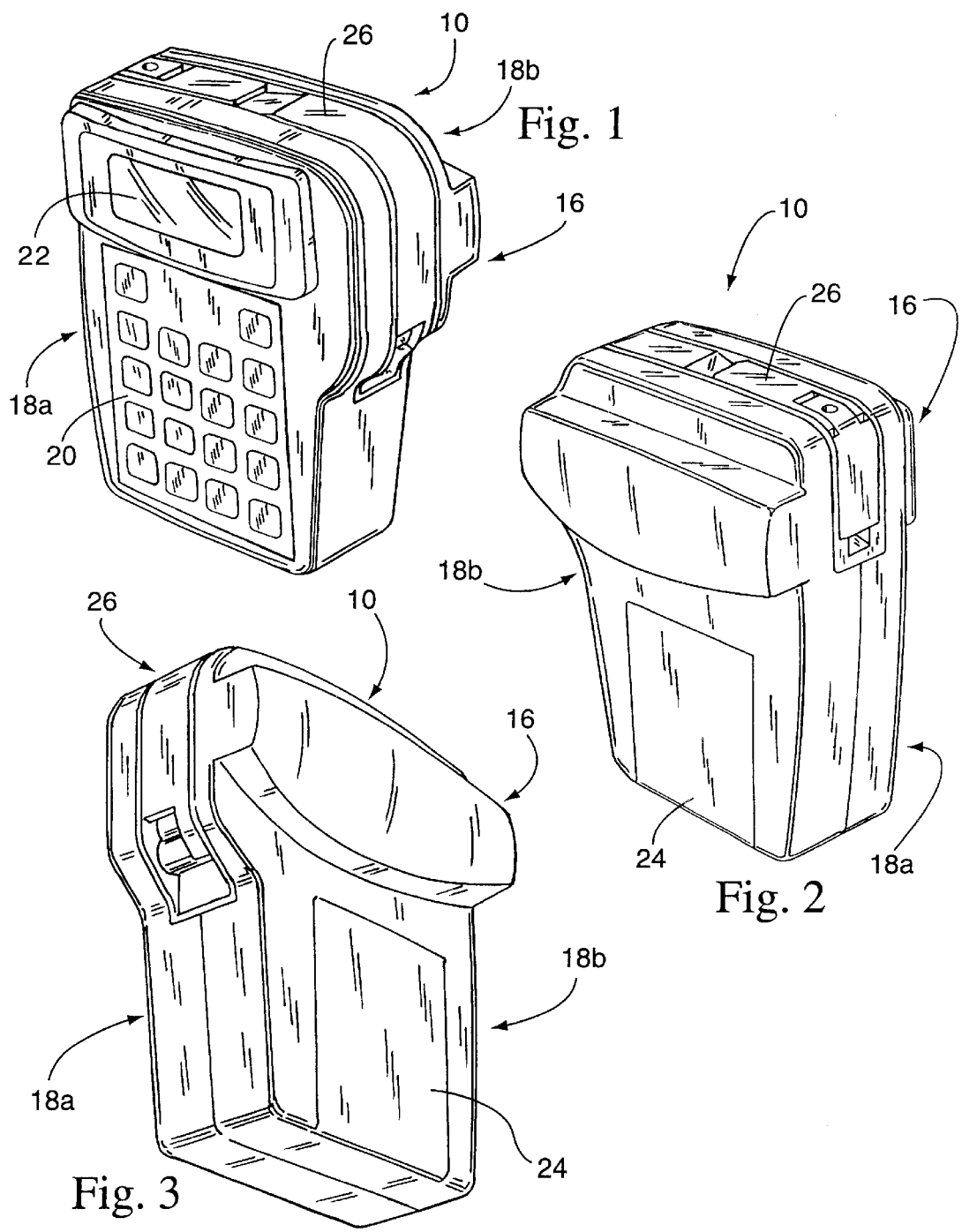

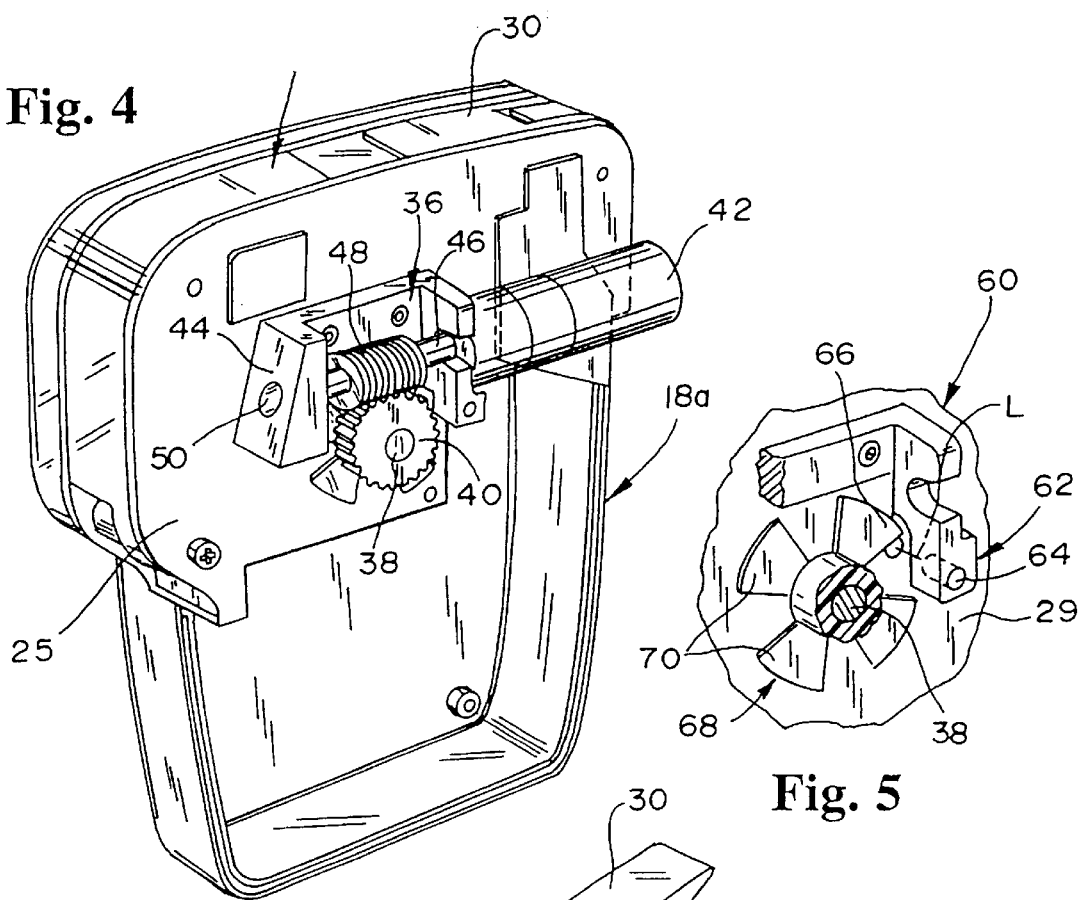
Fig. 4
Fig. 5
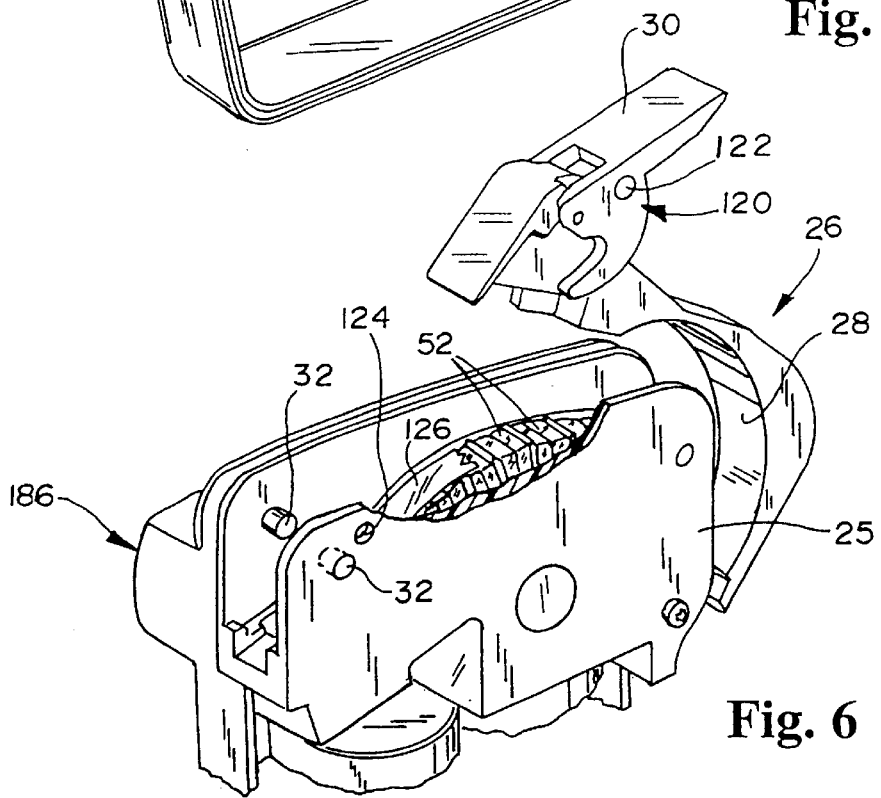
Fig. 6

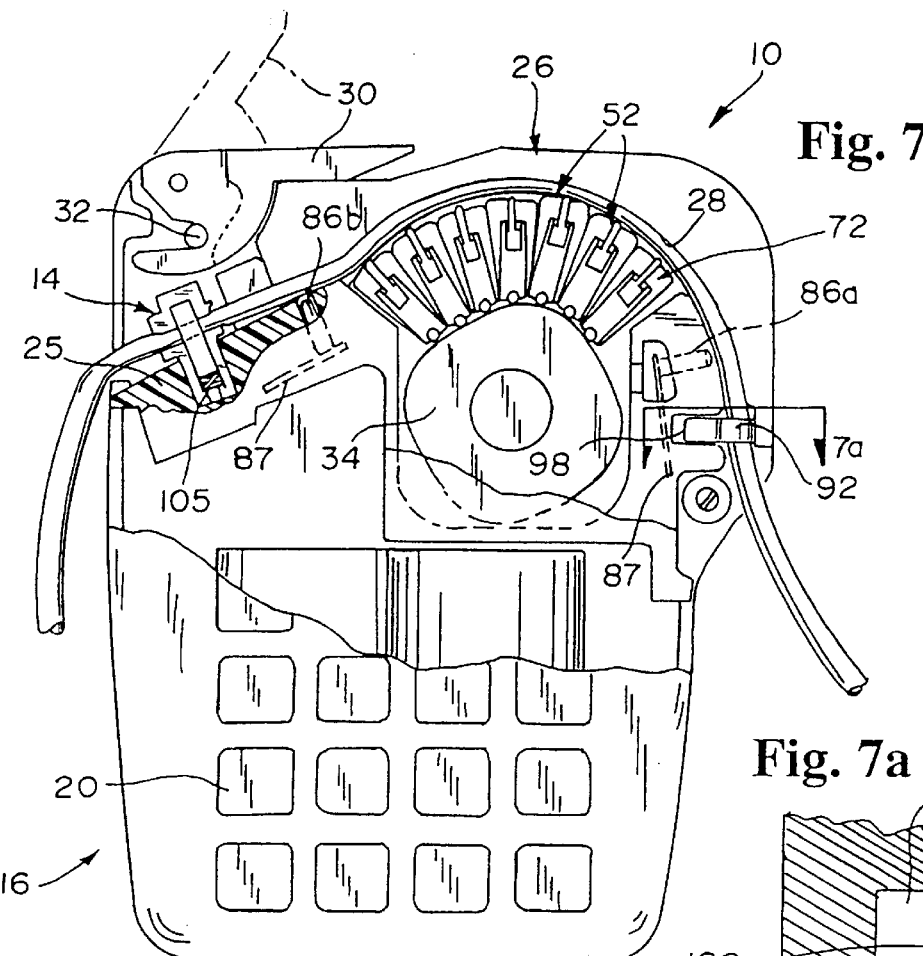
Fig. 7
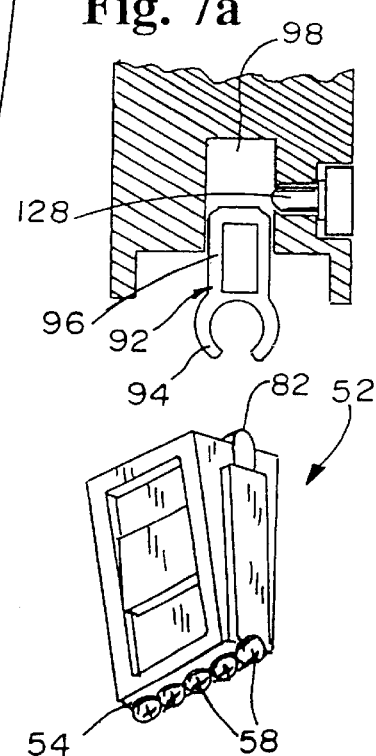
Fig. 7a
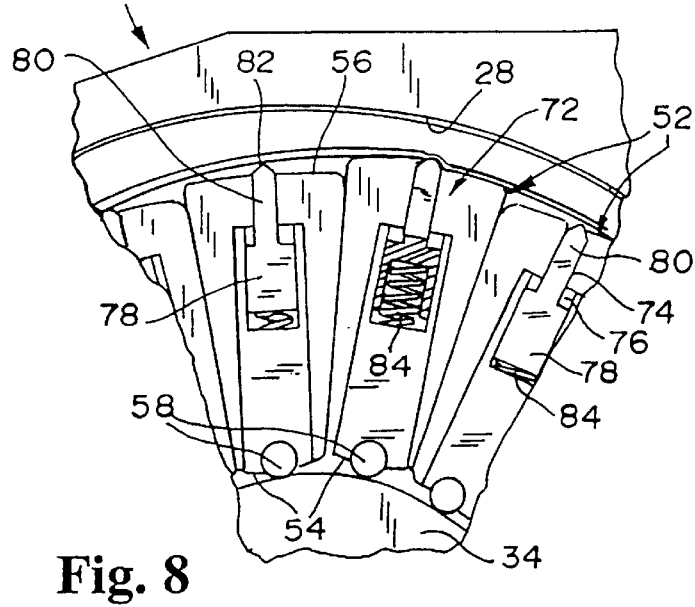
Fig. 8
Fig. 8a

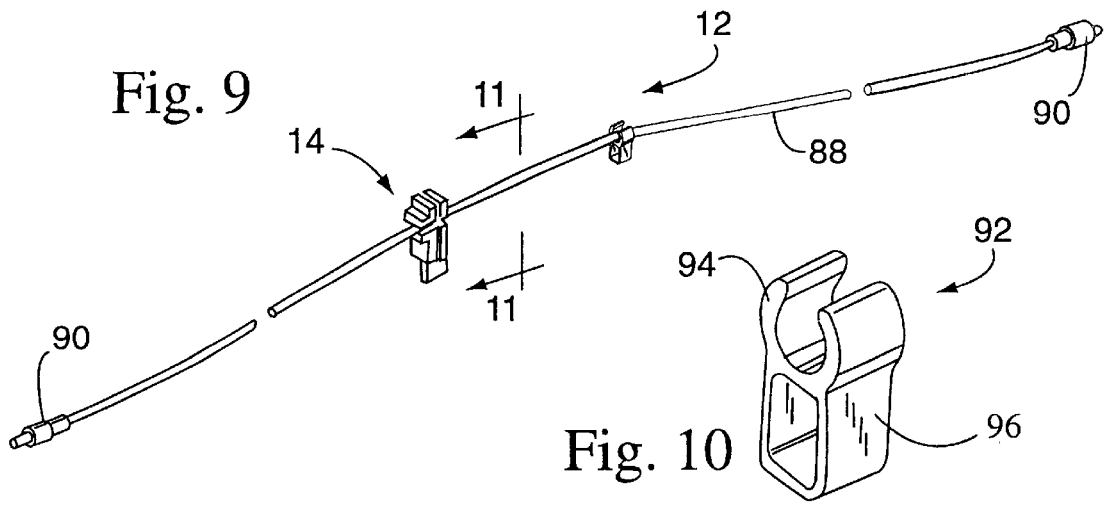
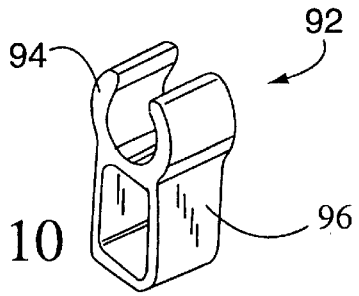
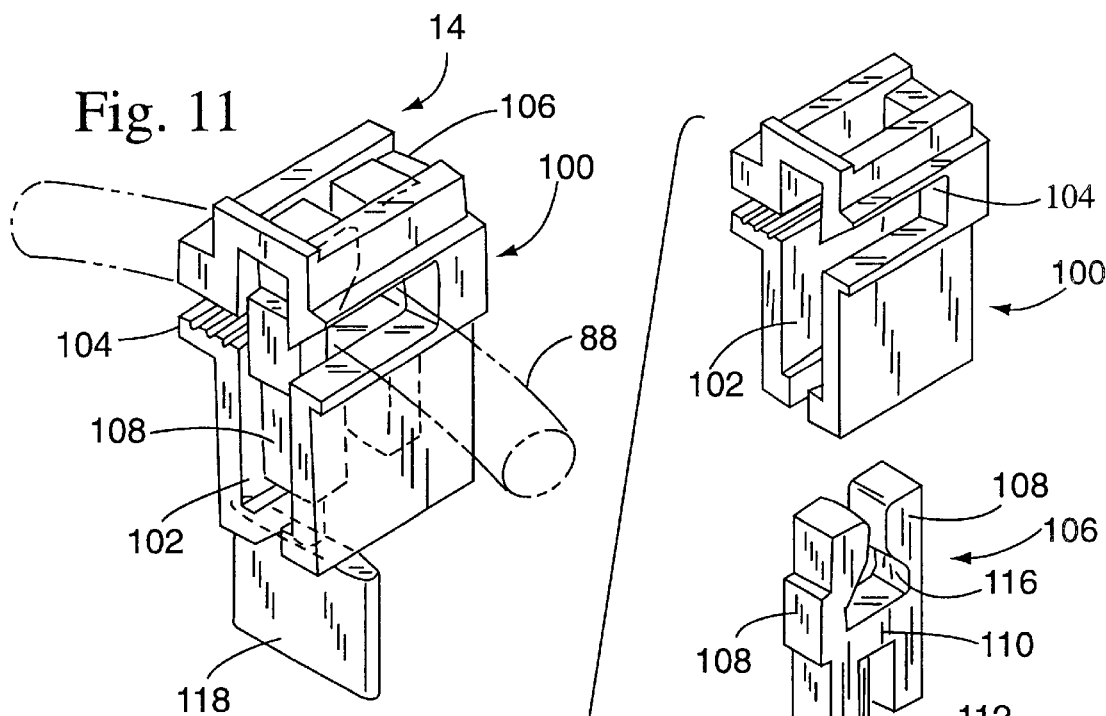
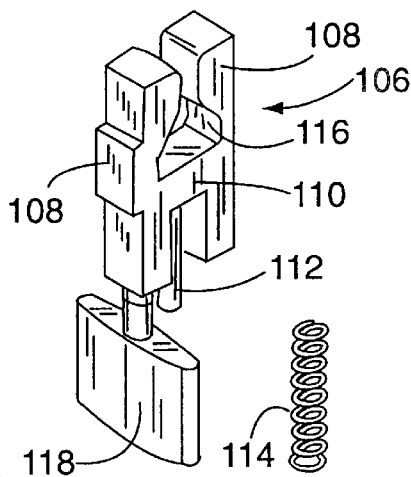

CURVILINEAR PERISTALTIC PUMP

This Application is a continuation of U.S. application Ser. No. 09/189,052 filed Nov. 9, 1998 now U.S. Pat. No. 6,164,921.

FIELD OF THE INVENTION

The present invention relates generally to medical infusion pumps, and more particularly to a curvilinear peristaltic pump having a plurality of cam driven pumping fingers which sequentially engage a segment of resilient tubing to facilitate the flow of a liquid therethrough.

BACKGROUND OF THE INVENTION

There is currently known in the prior art various types of peristaltic pumps which are typically used in medical applications for facilitating the metered intravenous infusion of a medicament into a patient. In addition to being used for infusion applications, prior art peristaltic pumps are also used for withdrawing fluids such as in a wound drainage system. These prior art pumps operate in a positive manner and are capable of generating substantial outlet pressures. The peristaltic pumps known in the prior art generally fall within one of two categories, i.e., linear peristaltic pumps and rotary peristaltic pumps. Conventional linear and rotary peristaltic pumps each typically have a section of resilient tubing positioned between a wall and a set of rollers or reciprocating pushers that progressively compress sections of the tubing to facilitate the pumping of a liquid therethrough.

More particularly, typical linear peristaltic pumps include those described in U.S. Pat. No. 2,877,714 (Sorg, et al.), U.S. Pat. No. 4,671,792 (Borsannyi), U.S. Pat. No. 4,893,991 (Heminway, et al.), and U.S. Pat. No. 4,728,265 (Canon). While generally effective, these prior art linear peristaltic pumps are large, complex and cumbersome, requiring a drive shaft parallel to a resilient tube and a plurality of cams along the drive shaft to move respective ones of a plurality of pushers toward and away from the tube.

Rotary peristaltic pumps known in the prior art generally disposed a resilient tube along a circular path, with a plurality of rollers mounted around the circumference of a circular rotor sequentially rolling along the tube to occlude the same and force liquid therethrough. Typical rotary peristaltic pumps include those described in U.S. Pat. No. 4,886,431 (Soderquist, et al.) and U.S. Pat. No. 3,172,367 (Kling). Though also generally effective, these pumps often have relatively low efficiencies and impose high shear and tension stresses on the tube, thus causing internal tube wall erosion or spallation. As a result, the tube may eventually be permanently deformed so that it becomes flattened into a more oval shape and carries less liquid, i.e., provides a decreased level of fluid flow therethrough.

In addition to the above-described linear and rotary peristaltic pumps, there is also known in the prior art another type of peristaltic pump having a tube arranged along a circular path with a cam member within the circle sequentially moving a plurality of blunt pushers or fingers outwardly to sequentially compress the tube from one end of the path to the other. These types of peristaltic pumps include those described in German Patent No. 2,152,352 (Gonner) and in Italian Patent No. 582,797 (Tubospir). Though these types of pumps tend to be less complex than linear peristaltic pumps, the pressure imposed by the blunt fingers typically reduces tube life, and sometimes causes internal tube wall erosion or spallation, thus resulting in particulate matter getting into the fluid stream. Additionally, tubes with different wall thicknesses cannot be accommodated by these particular prior art pumps. In this respect, with thinner than standard tubes, the fingers will not properly occlude the tube. Conversely, with thicker than standard tubes, the tube will close prematurely and be subject to excessive compression, thereby requiring higher cam drive power and causing excessive wear on the cam and tube.

In recognition of the deficiencies associated with the prior art peristaltic pumps described above, Applicant developed the curvilinear peristaltic pump disclosed in U.S. Pat. No. 5,575,631 (Jester) and U.S. Pat. No. 5,683,233 (Moubayed, et al) and PCT Application No. PCT/US97/03676 (Moubayed, et al.), the disclosures of which are incorporated herein by reference. This particular curvilinear peristaltic pump of the Applicant constituted an improvement over those known in the prior art by providing greater simplicity, small size, low drive power requirements and the ability to accommodate resilient tubes of varying wall thickness while reducing wear and internal erosion of the resilient tube. More particularly, this particular curvilinear peristaltic pump of the Applicant comprises a concave, curved platen for supporting a resilient tube, a multi-lobe cam rotatable about the center of the platen concavity, and a plurality of pump fingers which ride on the cam as cam followers and are guided to move in a radial direction toward and away from the platen. When the cam is rotated, the pump finger closest to the highest area (widest lobe) on the cam in the direction of rotation is moved outwardly in a radial direction to squeeze the tube against the platen. As the cam continues to rotate, the succeeding pump finger squeezes the tube as the preceding pump finger occludes the same, thus forcing the liquid in the tube to flow in the direction of cam rotation. As the cam rotation continues, the subsequent pump fingers sequentially squeeze the tube to push liquid and then occlude the tube, with the pump finger just behind the lobe moving away from the tube and allowing the same to expand and fill with the liquid.

Though this curvilinear peristaltic pump of the Applicant overcomes many of the deficiencies of the prior art peristaltic pumps, the design features of such pump give rise to certain inefficiencies in its operation. In particular, the motor, pulley and drive belt used to rotate the cam create a susceptibility for slight amounts of forward rotation or reverse rotation (roll back) of the cam upon the deactivation of the motor. Such slight forward or reverse rotation of the cam results in the engagement of the pump fingers to the tube in a manner causing an undesirable positive flow or backflow of liquid therewithin subsequent to the deactivation of the motor. As such, in this curvilinear peristaltic pump of the Applicant, power must be continuously supplied to the motor for purposes of preventing any unwanted rotation of the cam. As will be recognized, the need to constantly maintain power to the motor substantially increases its power consumption (e.g., reduces the life of any batteries used to supply power to the motor).

In addition to the foregoing, in Applicant's existing curvilinear peristaltic pump, a "pump cycle" occurs when the first through the last pump fingers along the tube move toward and away from the platen. During each "pump cycle", the engagement of the pump fingers against the tube in the above-described manner forces liquid therethrough. However, due to the configuration of the cam and the inability of the drive unit to selectively adjust the rotational speed thereof, there is a "dead pump phase" between the pump cycles in Applicant's existing curvilinear peristaltic pump wherein liquid is not being forced through the tube. As will be recognized, it is significantly more desirable if the liquid were to flow through the tube at a more uniform, steady rate. The operational efficiency of Applicant's existing curvilinear peristaltic pump would also be increased if it were to include structures which stabilize the length of the tube in the pump chamber and prevent a backflow of liquid within the tube upon a discontinuation of positive liquid pressure therewithin. The present invention addresses and overcomes the deficiencies of Applicant's existing curvilinear peristaltic pump, as well as the other peristaltic pumps currently known in the prior art.

SUMMARY OF THE INVENTION

In accordance with the present invention, there is provided a curvilinear peristaltic pump for facilitating the pumping of a liquid through a length of resilient tubing. The pump comprises a housing including a pair of housing halves which are attached to each other. In addition to the housing, the pump comprises a platen member which is pivotally connected to the housing and movable between an operative position and a non-operative position relative thereto. The platen member defines an arcuate, generally concave inner surface, and includes an over-the-center latch mechanism for maintaining the same in its operative position relative to the housing.

The present pump further comprises a rotatable cam which is disposed within the housing and rotatable about the approximate center of the concavity of the inner surface of the platen member. The rotation of the cam is facilitated by a drive unit of the pump which is also disposed within the housing. The drive unit is mechanically coupled to the cam such that the activation of the drive unit results in the concurrent rotation of the cam in a first direction, and the deactivation of the drive unit maintains the cam in a set position. In the preferred embodiment, the drive unit comprises a cam shaft which extends from the cam and includes a worm gear attached thereto. In addition to the cam shaft and worm gear, the drive unit comprises an electric motor having a rotatable motor shaft extending therefrom which includes a worm mounted thereto. The worm is itself cooperatively engaged to the worm gear. Importantly, the engagement between the worm and the worm gear results in the rotation of the cam in the first direction upon the activation of the motor, with such engagement also eliminating any rotation of the cam upon the deactivation of the motor. The electric motor of the drive unit is preferably powered by multiple batteries (e.g., C-cell batteries) which are stored within the housing.

The present pump further comprises a plurality of pump fingers which are movably attached to the housing and are arranged in side-by-side relation to each other so as to define a row. Each of the pump fingers has a first end which is cooperatively engaged to the cam and a second end which is disposed in spaced relation to the platen member. Attached to the housing is a pliable, transparent membrane of the pump which covers the second ends of the pump fingers and is used to prevent moisture from leaking into the interior of the housing. As such, the second ends of the pump fingers are covered by the membrane, and are disposed in substantially equidistantly spaced relation to the inner surface of the platen member when in its operative position. The membrane is exposed when the platen member is in its non-operative position. Each of the pump fingers preferably includes a plurality of roller members rotatably mounted within and protruding from the first end thereof, with the pump fingers being cooperatively engaged to the cam via the roller members.

In the present pump, the cam is configured to sequentially move the pump fingers radially outwardly toward and inwardly away from the inner surface of the platen member when rotated in the first direction by the drive unit. In this respect, a portion of the tubing may be extended between the inner surface of the platen member and the membrane (and hence the second ends of the pump fingers) such that the sequential movement of the pump fingers toward and away from the platen member results in liquid within the tubing being pumped in the first direction of rotation of the cam. As will be recognized, since the pumping of the liquid through the tubing is dependent upon the sequential engagement of the pump fingers thereagainst and the movement of the pump fingers is dependent upon the rotation of the cam, the deactivation of the motor which eliminates any rotation of the cam due to the engagement between the worm and the worm gear assists in preventing any positive flow or backflow of liquid through the tubing.

In the present pump, the sequential movement of each of the pump fingers of the row toward and away from the platen member by the rotation of the cam defines a pump cycle. In the preferred embodiment, the cam is profiled or shaped so as to act against the first ends of the pump fingers in a manner causing the second ends thereof to engage the tubing such that the flow rate of liquid therethrough is substantially constant throughout each pump cycle. Such constant flow rate is achieved by forming the cam as a four lobe cam. In addition to the cam being shaped to provide a substantially constant flow rate throughout each pump cycle, the pump of the present invention is preferably provided with a motor speed control unit which is operable to selectively increase and decrease the rotational speed of the cam at prescribed intervals. More particularly, the motor speed control unit is operable to increase the rotational speed of the cam in the first direction between pump cycles for purposes of substantially eliminating the dead pumping phase which normally exists between pump cycles.

The motor speed control unit of the present pump is disposed within the housing and comprises an optical sensor which is electrically connected to the motor. The optical sensor is adapted to transmit a beam of light and sense any interruptions therein. In this respect, the optical sensor includes a light beam transmitter which is adapted to generate a beam of light, and a light beam receiver which is adapted to receive or sense the beam of light generated by the light beam transmitter. In addition to the optical sensor, the motor speed control unit comprises an encoder wheel which is attached to the cam shaft and rotatable thereby. The encoder wheel includes a plurality of encoder arms extending radially therefrom and is oriented relative to the optical sensor such that the encoder arms intermittently interrupt the beam of light during the rotation of the encoder wheel by the cam shaft. Importantly, the number and size of the encoder arms is selected such that interruptions in the beam of light caused thereby correspond to pump cycles, with the optical sensor being operable to determine the beginning and end of each pump cycle and increase the power to the motor and hence the rotational speed of the cam between pump cycles. As will be recognized, the increased rotational speed of the cam between pump cycles substantially reduces the dead pump phase, thereby providing a more uniform rate of liquid flow through the tubing.

The present pump further comprises a plurality of pinch members which are movably attached to respective ones of the pump fingers and protrude from the second ends thereof. Each of the pinch members is biased radially outwardly toward the inner surface of the platen member and operable to substantially occlude the tubing when the pump finger to which it is attached is moved radially outwardly to a position closest to the inner surface of the platen member. To facilitate the attachment of a pinch member thereto, each of the pump fingers is provided with a transverse slot which is disposed within the second end thereof and transitions into a transverse cavity therewithin. Each of the pinch members preferably comprises a base portion which is disposed within the transverse cavity and a finger portion which extends from the base portion into the transverse slot. The finger portion defines a finger tip which protrudes from the second end of the pump finger. Extending between the base portion and the wall of the transverse cavity disposed furthest from the finger portion is a biasing spring of the pinch member. The present pump further comprises a pair of pressure sensor members which are oriented within the housing adjacent respective ends of the row of pump fingers for engaging the tubing and generating electrical signals corresponding to the degree of compression or expansion thereof when acted upon by the pump fingers and pinch members.

The pump constructed in accordance with the present invention is preferably used in conjunction with a tubing assembly which is releasably attachable to the housing. The tubing assembly comprises a length of substantially straight, resilient tubing which is preferably fabricated from polyvinyl chloride (PVC). Attached to the tubing is a tubing locator pin and a shut-off valve which is operable to selectively obstruct the flow of liquid through the tubing in a direction opposite the first direction of rotation of the cam. The tubing locator pin and the shut-off valve are removably insertable into respective ones of a pair of recesses formed within the housing outwardly of each of the opposed ends of the row of pump fingers. Importantly, the tubing locator pin and the shut-off valve are attached to the tubing at locations whereat a portion of the tubing is extended over the second ends of the pump fingers when the tubing locator pin and the shut-off valve are removably inserted into their respective recesses within the housing. When the platen member is in its operative position, the tubing is extended between the second ends of the pump fingers and the platen member such that the sequential movement of the pump fingers toward and away from the platen member results in liquid within the tubing being pumped in the first direction of rotation of the cam.

In the present pump, the tubing locator pin and the shut-off valve of the tubing assembly are removably insertable into their respective recesses within the housing when the platen member is in its non-operative position. As indicated above, the portion of the tubing extended over the second ends of the pump fingers by the insertion of the tubing locator pin and the shut-off valve into their respective recesses within the housing is captured between the second ends and the inner surface when the platen member is moved to its operative position.

In the preferred embodiment, the shut-off valve of the tubing assembly itself comprises a valve body having an opening therein for permitting the passage of the tubing therethrough. Movably attached to the valve body is a pinch arm which is engagable to the tubing passing through the opening. The pinch arm is movable between an open position whereat the tubing passing through the valve body is only partially collapsed thereby and not compressed by the pinch arm which allows for the flow of liquid through the tubing, and a closed position whereat the tubing passing through the valve body is completely collapsed by the pinch arm acting thereagainst which prevents the flow of liquid through the tubing. The shut-off valve further includes a biasing member which normally biases the pinch arm to the closed position, with the biasing member preferably comprising a spring which extends between the valve body and the pinch arm. The pinch arm of the shut-off valve itself includes a breakable detent tab formed thereon which maintains the pinch arm in its open position. The removal or breakage of the detent tab from the pinch arm results in the movement of the pinch arm to its closed position.

In the present pump, the platen member is sized and configured to move the pinch arm from its closed position to its open position when the platen member is moved to its operative position. Additionally, the platen member is pivotally connected to the housing at a location whereat the movement of the platen member from its non-operative position to its operative position results in the occlusion of the tubing by at least one of the pinch members prior to the movement of the pinch arm of the shut-off valve from its closed position to its open position by the platen member.

In addition to the above-described pressure sensor members, the present pump is provided with a platen sensor which is disposed within the housing and operable to detect when the platen member is in the operative position. More particularly, the platen sensor comprises a Hall effect sensor which includes a magnet disposed within the over-the-center latch mechanism of the platen member. In addition to the magnet, the platen sensor includes a magnetic field detector which is disposed within the housing. The magnet and the magnetic field detector are oriented so as to be disposed directly adjacent each other when the platen member is in its operative position. The pump also includes a tubing sensor which is disposed within the housing and operable to detect when the tubing is extended over the membrane. More particularly, whereas the platen sensor is tripped by the movement of the platen member to its operative position, the tubing sensor is tripped by the insertion of the tubing locator pin into its corresponding recess within the housing. In the preferred embodiment, the platen sensor and the tubing sensor are electrically connected in series such that the drive unit may not be activated until the tubing is extended over the membrane and the platen member is in its operative position.

Advantageously, the tubing locator pin and shut-off valve of the tubing assembly may be added or attached to lengths of resilient tubing of differing diameters. Additionally, the use of off-the-shelf straight line, continuous PVC tubing in the present tubing assembly as opposed to a segment of silicone tubing having segments of PVC tubing adhesively secured thereto as is required by many prior art peristaltic pumps substantially reduces the costs associated with the present tubing assembly, in addition to providing increased reliability due to the absence of any adhesive joints. In the tubing assembly, the shut-off valve attached to the tubing is maintained in its open position during shipment so as not to cause any premature deformation in the tubing. When the present pump and accompanying tubing assembly are ready for use, the detent tab is broken away from the pinch arm of the shut-off valve, thus causing the same to assume its normally closed position upon the tubing.

BRIEF DESCRIPTION OF THE DRAWINGS

These, as well as other features of the present invention, will become more apparent upon reference to the drawings wherein:

FIG. 1 is a front, top perspective view of the peristaltic pump of the present invention;

FIG. 2 is a rear, top perspective view of the peristaltic pump of the present invention;

FIG. 3 is a rear, bottom perspective view of the peristaltic pump of the present invention;

FIG. 4 is a perspective view of the worm gear drive unit of the present peristaltic pump;

FIG. 5 is a perspective view of the motor speed control unit of the present peristaltic pump;

FIG. 6 is a perspective view of the platen member of the present peristaltic pump, illustrating the manner it is engageable to the housing thereof;

FIG. 7 is a partial cross-sectional view of the present peristaltic pump, illustrating the manner in which the tubing assembly thereof is operatively captured between the pump fingers and platen member of the pump;

FIG. 7a is a partial cross-sectional view illustrating the manner in which the tubing sensor of the present peristaltic pump is tripped by the insertion of the tubing locator pin of the tubing assembly into the housing;

FIG. 8 is a partial cross-sectional view of the pump fingers of the present peristaltic pump, illustrating the manner in which the pinch members thereof engage the tubing of the tubing assembly;

FIG. 8a is a perspective view of one of the pump fingers of the present peristaltic pump;

FIG. 9 is a perspective view of the tubing assembly of the present peristaltic pump;

FIG. 10 is a perspective view of the tubing locator pin of the tubing assembly shown in FIG. 9;

FIG. 11 is a perspective view of the shut-off valve of the tubing assembly taken along line 11—11 of FIG. 9;

FIG. 12 is an exploded view of the shut-off valve shown in FIG. 11;

DETAILED DESCRIPTION OF THE PREFERRED EMBODIMENT

Figure 13:
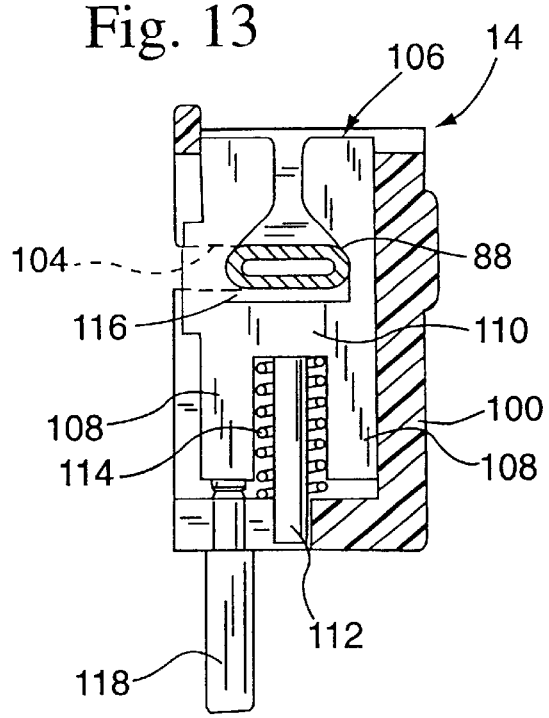
FIG. 13 is a cross-sectional view of the shut-off valve as in its open position.

Referring now to the drawings wherein the showings are for purposes of illustrating a preferred embodiment of the present invention only, and not for purposes of limiting the same, FIGS. 1–3 perspectively illustrate the curvilinear peristaltic pump 10 constructed in accordance with the present invention. The present pump 10 is preferably used in conjunction with a tubing assembly 12 which is shown in FIG. 9 and will be described in more detail below. The tubing assembly 12 itself is provided with a novel and unique shut-off valve 14 of the present invention which is shown in FIGS. 11–14 and will also be described in more detail below.

PERISTALTIC PUMP

The present pump 10 is adapted to facilitate the pumping of a liquid through the tubing assembly 12, and comprises a housing 16. The housing 16 includes a front housing half 18a and a back housing half 18b which are rigidly attached to each other through the use of fasteners such as screws, though alternative attachment methods may also be employed in relation thereto. As seen in FIG. 1, the front housing half 18a is provided with a keypad 20 and a visual display 22, the use of which will be discussed in more detail below. The back housing half 18b is provided with a removable door 24 for accessing a battery storage compartment within the interior of the housing 16. The front and back housing halves 18a, 18b are preferably fabricated from a plastic material, though alternative lightweight materials may be used for the fabrication thereof. In addition to the front and back housing halves 18a, 18b, the housing 16 comprises a support member 25 which defines a channel having a generally U-shaped cross-sectional configuration. The support member 25 is attached to the front and back housing halves 18a, 18b such that the channel defined thereby extends longitudinally between the upper ends of the front and back housing halves 18a, 18b.

Referring now to FIGS. 1–4 and 6, the pump 10 further comprises a platen member 26 which is pivotally connected to the support member 25 of the housing 16 and moveable between an operative position (as shown in FIGS. 1–3, 7 and 8) and a non-operative position (as shown in FIG. 6) relative thereto. The platen member 26 defines an arcuate, generally concave inner surface 28. When the platen member 26 is in its operative position, it resides within the channel defined by the support member 25, with the inner surface 28 being shielded thereby. As best seen in FIGS. 6 and 7, the platen member 26 is provided with an over-the-center latch mechanism 30 on the end thereof opposite that pivotally connected to the support member 25. The latch mechanism 30 is cooperatively engagable to a pair of latch pins 32 protruding from respective ones of opposed inner surfaces of the support member 25 into the channel defined therebetween. As will be recognized, the engagement of the latch mechanism 30 to the latch pins 32 maintains or locks the platen member 26 within its operative position.

As further seen in FIG. 6, the pump 10 includes a platen sensor 120 which is operable to detect when the platen member 26 is in its operative position. In the preferred embodiment, the platen sensor 120 is a Hall effect sensor which comprises a magnet 122 disposed within the over-the-center latch mechanism 30 of the platen member 26. In addition to the magnet 122, the platen sensor 120 includes a magnetic field detector 124 which is disposed within the support member 25 in close proximity to one of the latch pins 32 protruding therefrom. The magnetic field detector 124 is oriented so as to be disposed directly adjacent the magnet 122 when the platen member 26 is moved to its operative position and the latch mechanism 30 engaged to the latch pins 32. The use of the platen sensor 120 will be discussed in more detail below.

Referring now to FIG. 7, the pump 10 further comprises a rotatable cam 34 which is disposed within the interior of the housing 16 and rotatably mounted to the support member 25. More particularly, the cam 34 is mounted to the support member 25 so as to be rotatable about an axis which extends through the approximate center of the concavity of the arcuate inner surface 28 of the platen member 26 when the platen member 26 is in its operative position.

Referring now to FIG. 4, the rotation of the cam 34 is facilitated by a drive unit 36 of the pump 10 which is also disposed within the interior of the housing 16 and attached to the support member 25. The drive unit 36 is mechanically coupled to the cam 34 such that the activation of the drive unit 36 results in the concurrent rotation of the cam in a first direction (i.e., the counter-clockwise rotation of the cam 34 when observed from the perspective shown in FIG. 7), and the deactivation of the drive unit 36 maintains the cam in a set position. In the preferred embodiment, the drive unit 36 comprises a cam shaft 38 which extends from the cam 34. Attached to the cam shaft 38 is a worm gear 40 of the drive unit 36. In addition to the cam shaft 38 and worm gear 40, the drive unit 36 comprises a variable speed electric motor 42 which is attached to the support member 25 via a motor mount 44. Extending from the electric motor 42 is a rotatable motor shaft 46 which includes a worm 48 mounted thereto. The distal end of the motor shaft 46 is rotatably mounted within a bearing disposed within an aperture 50 extending through a portion of the motor mount 44. The worm 48 is itself cooperatively engaged to the worm gear 40.

In the drive unit 36, the engagement between the worm 48 and the worm gear 40 results in the rotation of the cam 34 in the first direction upon the activation of the motor 42. Such engagement also eliminates any rotation of the cam 34 upon the deactivation of the motor 42, the significance of which will be discussed in more detail below. The motor 42 of the pump 10 is electrically connected to and powered by a multiple batteries which are stored within the interior of the housing 16 and accessible via the access door 24 provided on the back housing half 18b.

Referring now to FIGS. 6–8 and 8a, the pump 10 of the present invention further comprises a plurality of pump fingers 52 which are movably attached to the support member 25 and are arranged in side-by-side relation to each other so as to define an arcuate row. Each of the pump fingers 52 has a first end 54 which is cooperatively engaged to the cam 34 and a second end 56 which is disposed in spaced relation to the platen member 26 when the same is in its operative position. The pump 10 also includes a pliable membrane 126 which is preferably fabricated from a transparent or translucent material and is attached to the support member 25 so as to cover the second ends 56 of the pump fingers 52. Importantly, the membrane 126 functions to prevent any moisture from leaking into the interior of the housing 16. As such, the second ends 56 of the pump fingers 52 are covered by the membrane 126, and are disposed in substantially equidistantly spaced relation to the arcuate inner surface 28 of the platen member 26 when in its operative position. The membrane 126 is exposed (as shown in FIG. 6) when the platen member 26 is in its non-operative position. The membrane is preferably formed to have a thickness of about 0.007 inches. As best seen in FIGS. 7, 8 and 8a, each of the pump fingers 52 preferably includes a plurality of roller members 58 rotatably mounted within and protruding from the first end 54 thereof. The roller members 58 of each pump finger 52 are arranged in a row. The pump fingers 52 are cooperatively engaged to the cam 34 via the roller members 58. As will be recognized, since the roller members 58 freely roll on the camming surfaces of the cam 34, wear on such camming surfaces is substantially reduced.

Referring now to FIG. 5, the present pump 10 further comprises a motor speed control unit 60 which is operable to selectively increase and decrease the rotational speed of the cam 34 at prescribed intervals for reasons which will be discussed in more detail below. The motor speed control unit 60 is disposed within the interior of the housing 16 and comprises an optical sensor 62 which is attached to the motor mount 44 and electrically connected to the motor 42. The optical sensor 62 is adapted to transmit a beam of light L and sense any interruptions therein. In this respect, the optical sensor 62 includes a light beam transmitter 64 which is adapted to generate the beam of light L, and a light beam receiver 66 which is adapted to receive or sense the beam of the light L generated by the light beam transmitter 64.

In addition to the optical sensor 62, the motor speed control unit 60 comprises a shutter or encoder wheel 68 which is attached to the cam shaft 38 and rotatable thereby. The optical sensor 62 and encoder wheel 68 collectively define an optical encoder. The encoder wheel 68 includes four (4) encoder arms 70 extending radially therefrom in equidistantly spaced intervals of approximately 90 degrees. Importantly, the encoder wheel 68 is oriented relative to the optical sensor 62 such that the encoder arms 70 will intermittently interrupt the beam of light L during the rotation of the encoder wheel 68 by the cam shaft 38. As will also be discussed in more detail below, the number and size of the encoder arms 70 is selected such that interruptions in the beam of light L caused thereby correspond to pump cycles of the pump 10, with the optical sensor 62 being operable to determine the beginning and end of each pump cycle and increase the power to the motor 42 and hence the rotational speed of the cam 34 between pump cycles.

Referring now to FIGS. 7 and 8, the pump 10 further comprises a plurality of pinch members 72 which are movably attached to respective ones of the pump fingers 52 and protrude from the second ends 56 thereof. To facilitate the attachment of a pinch member 72 thereto, each of the pump fingers 52 is provided with a transverse slot 74 which is disposed within the second end 56 thereof and transitions into a transverse cavity 76 therewithin. Each of the pinch members 72 preferably comprises a base portion 78 which is disposed within the transverse cavity 76 and a finger portion 80 which extends from the base portion 78 into the transverse slot 74. The finger portion 80 defines a finger tip 82 which protrudes from the second end 56 of a respective one of the pump fingers 52. Extending between the base portion 78 and the wall of the respective transverse cavity 76 disposed furthest from the finger portion 80 is a biasing spring 84 of the pinch member 72. The biasing springs 84 function to bias the pinch members 72 radially outwardly toward the inner surface 28 of the platen member 26 when the platen member 26 is in its operative position for reasons which will also be discussed in more detail below.

Referring now to FIG. 7, the present pump 10 further comprises a pair of pressure sensor members 86a, 86b, portions of which protrude from the support member 25 adjacent respective ends of the row of pump fingers 52. Each of the pressure sensor members 86a, 86b includes a beam 87 having a strain gauge disposed thereon. The functionality of the pressure sensor members 86a, 86b will also be described in more detail below.

TUBING ASSEMBLY

Referring now to FIGS. 7–14, the pump 10 constructed in accordance with the present invention is preferably used in conjunction with the tubing assembly 12 which is releasably attachable to the support member 25 of the housing 16. The tubing assembly 12 comprises a length of substantially straight, resilient tubing 88 which is preferably fabricated from polyvinyl chloride (PVC). Attached to each of the opposed ends of the tubing 88 are respective ones of a pair of connectors 90, such as standard Luer connectors. Additionally, attached to the tubing 88 is a tubing locator pin 92 (shown in FIG. 10) and the shut-off valve 14 (shown in FIGS. 11–14) which is operable to selectively obstruct the flow of liquid through the tubing. As seen in FIG. 10, the tubing locator pin 92 includes a generally C-shaped attachment portion 94 which is adapted to receive and functionally engage the tubing 88 in a manner maintaining the tubing locator pin 92 in a desired location thereupon. In addition to the attachment portion 94, the tubing locator pin 92 includes a mounting portion 96 which is receivable into a complementary recess 98 formed within the support member 25 adjacent the location whereat the platen member 26 is pivotally connected thereto.

Referring now to FIG. 7a, the present pump 10 further comprises a tubing sensor 128 which is disposed within the recess 98 formed within the support member 25. As will be discussed in more detail below, the tubing sensor 128 is operable to detect when the tubing assembly 12 is properly engaged to the support member 25, and is tripped by the insertion of the tubing locator pin 92 into the recess 98.

Referring now to FIGS. 11–14, the shut-off valve 14 of the tubing assembly 12 comprises a valve body 100. The valve body 100 defines a first slot 102 extending longitudinally therethrough and a second slot 104 extending laterally therethrough in generally perpendicular or transverse relation to the first slot 102. As such, the first and second slots 102, 104 collectively form a generally T-shaped pattern within the valve body 100. The lower portion of the valve body 100 is insertable into a complementary recess 105 formed within the support member 25 adjacent the end thereof opposite that including the recess 98 formed therein.

Figure 14:
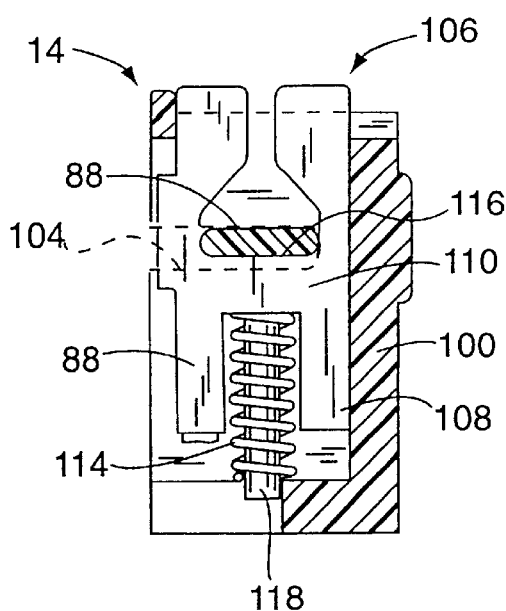
FIG. 14 is a cross-sectional view of the shut-off valve as in its closed position.

In addition to the valve body 100, the shut-off valve 14 comprises a pinch arm 106 which has a generally H-shaped configuration and includes an opposed pair of side bar portions 108 which are interconnected by a cross bar portion 110 integrally connected thereto and extending generally perpendicularly therebetween. Formed on and extending generally perpendicularly from one side of the cross bar portion 110 is a post portion 112 of the pinch arm 106 which has a generally cylindrical configuration. As seen in FIGS. 12–14, the post portion 112 is sized having a length such that the distal end thereof protrudes beyond the lower ends of the side bar portions 108. Disposed on the post portion 112 is a biasing spring 114 of the shut-off valve 14. As further seen in FIGS. 12–14, the surface of the cross bar portion 110 opposite that having the post portion 112 extending therefrom and portions of the inner surfaces of the side bar portions 108 collectively define an opening 116 of the pinch arm 106. Additionally, as seen in FIGS. 11–13, when the pinch arm 106 is initially formed, the same is provided with a breakable detent tab 118 which is integrally connected to the lower end of one of the side bar portions 108, and thus is disposed adjacent the post portion 112. The use of the detent tab 118 will be described in more detail below. Those of ordinary skill in the art will recognize that the valve body 100 of the shut-off valve 14, as well as the pinch arm 106 thereof, may be provided in shapes other than for those described above.

In the shut-off valve 14, the pinch arm 106, including the biasing spring 114 mounted to the post portion 112, is movably attached to the valve body 100 via the receipt of the pinch arm 106 into the first slot 102. When the pinch arm 106 is properly inserted into the first slot 102, the upper ends of the side bar portions 108 thereof protrude from the upper end of the first slot 102 as seen in FIGS. 13 and 14, with the distal end of the post portion 112 extending into a reduced width section of the first slot 102 defined at the bottom end thereof. Additionally, the opening 116 defined by the pinch arm 106 is oriented so as to be in substantial alignment with the second slot 104 of the valve body 100. When the pinch arm 106 is initially attached to the valve body 100, the detent tab 118 engages the bottom end of the valve body 100 in a manner which maintains the biasing spring 114 in a state of compression and prevents the pinch arm 106 from reaching its maximum limit of upward travel.

In the tubing assembly 12, the shut-off valve 14 is attached to the tubing 88 via the advancement of the tubing 88 through the second slot 104 and opening 116. As seen in FIG. 13, the second slot 104 of the valve body 100 is sized relative to the tubing 88 such that the wall of the tubing 88 and hence the lumen defined thereby is partially collapsed by the valve body 100 when the tubing 88 is advanced through the second slot 104 and opening 116. As will be recognized, the compression of the tubing 88 by the valve body 100 facilitates the frictional retention of the shut-off valve 14 at a prescribed location upon the tubing 88.

In the tubing assembly 12, the shut-off valve 14, and in particular its pinch arm 106, is moveable between an open position (as shown in FIG. 13) and a closed position (as shown in FIG. 14). When the pinch arm 106 is in its open position, the wall of the tubing 88 passing through the shut-off valve 14 is only partially collapsed by the valve body 100 and not compressed by the pinch arm 106. As such, the wall of the tubing 88 continues to define an open lumen which allows for the flow of liquid through the tubing 88. Conversely, when the pinch arm 106 is moved to its closed position, it acts against and applies compressive pressure to the wall of the tubing 88 in a manner completely collapsing the same and hence the lumen defined thereby. As will be recognized, the complete collapse of the tubing 88 facilitated by the movement of the pinch arm 106 to its closed position prevents the flow of liquid through the tubing 88. Since the tubing 88 is already partially collapsed by the passage thereof through the second slot 104, the total length of movement of the pinch arm 106 from its open position to its closed position whereat the tubing 88 is completely collapsed thereby is only about a few millimeters. The biasing spring 114 normally biases the pinch arm 106 to its closed position. The movement of the pinch arm 106 to its open position is accomplished by the application of pressure to the upper ends of the side bar portions 108 protruding from the upper end of the first slot 102 of the valve body 100 in an amount sufficient to overcome the biasing force exerted by the biasing spring 114 and move the pinch arm 106 toward the reduced width bottom end of the first slot 102.

In the tubing assembly 12, the shut-off valve 14 attached to the tubing 88 is preferably maintained in its open position during shipment so as not to cause any premature permanent deformation in the tubing 88. As indicated above, the engagement of the detent tab 118 against the valve body 100 maintains the pinch arm 106 in its open position in the manner shown in FIG. 13. When the pump 10 and accompanying tubing assembly 12 are ready for use, the detent tab 118 is fractured or broken away from the remainder of the pinch arm 106 by twisting it approximately ninety degrees, thus causing the pinch arm 108 to immediately assume its normally closed position relative to the tubing 88 as shown in FIG. 14.

As indicated above, the mounting portion 96 of the tubing locator pin 92 is removably insertable into the recess 98 of the support member 25, with the lower portion of the valve body 100 of the shut-off valve 14 being removably insertable into the recess 105 of the support member 25. As seen in FIG. 7, the recesses 98, 105 are formed within the support member 25 outwardly of each of the opposed ends of the row of pump fingers 52. As further seen in FIG. 7, in the tubing assembly 12, the tubing locator pin 92 and the shut-off valve 14 are attached to the tubing 88 at locations whereat a portion of the tubing 88 is extended over the membrane 126, and hence the second ends 56 of the pump fingers 52 (including the finger tips 82 protruding therefrom), when the tubing locator pin 92 and shut-off valve 14 are removably inserted into their respective recesses 98, 105.

As will be recognized, the tubing locator pin 92 and the shut-off valve 14 of the tubing assembly 12 are removably insertable into their respective recesses 98, 105 when the platen member 26 is in its non-operative position. As will be discussed in more detail below, the portion of the tubing 88 of the tubing assembly 12 extended over the second ends 56 of the pump fingers 52 by the insertion of the tubing locator pin 92 and the shut-off valve 14 into their respective recesses 98, 105 is captured between the second ends 56 (including the fingertips 82 of the pinch members 72 protruding therefrom) and the inner surface 28 when the platen member 26 is moved to its operative position.

In the tubing assembly 12, the tubing locator pin 92 and shut-off valve 14 may be added or attached to lengths of resilient tubing of differing diameters. Additionally, the use of off-the-shelf straight line, continuous PVC tubing in the present tubing assembly 12 as opposed to a segment of silicone tubing having segments of PVC tubing mechanically secured thereto as is required by many prior art peristaltic pumps substantially reduces the costs associated with the present tubing assembly 12, in addition to providing increased reliability thereto due to the absence of any mechanical joints therein.

PERISTALTIC PUMP USE AND OPERATION

Having thus described the structural attributes of the pump 10 and accompanying tubing assembly 12, the preferred manner of using the same will now be described with particular reference to FIGS. 6–8. In the following discussion, it will be recognized that when the tubing 88 is described as being extended over the second ends 56 of the pump fingers 52 (including the fingertips 82 of the pinch members 72 protruding therefrom), or between the second ends 56 and the inner surface 28 of the platen member 26, the tubing 88 is actually being extended over the membrane 126 or between the membrane 126 and the inner surface 28. Similarly, in any instance when the second ends 56 and/or fingertips 82 are described as acting against the tubing 88, the contact therebetween actually occurs via the membrane 126 which covers the second ends 56 and fingertips 82. However, those of ordinary skill in the art will recognize that the membrane 126 need not necessarily be included in the pump 10, and that the tubing 88 may be extended directly over the second ends 56 of the pump fingers 52 and fingertips 82 of the pinch members 72.

The pump 10 is used by initially moving the platen member 26 to its non-operative position as shown in FIG. 6. Thereafter, the tubing assembly 12 is releasably attached to the pump 12 via the insertion of the mounting portion 96 of the tubing locator pin 92 into the recess 98, and the insertion of the lower portion of the valve body 100 of the shut-off valve 14 into the recess 105. As previously explained, the shut-off valve 14 and tubing locator pin 92 are attached to the tubing 88 of the tubing assembly 12 at locations whereat the insertion thereof into respective ones of the recesses 98, 105 results in a portion of the tubing 88 being extended over the second ends 56 of the pump fingers 52 (including the finger tips 82 of the pinch members 72 protruding therefrom). The insertion of the tubing locator pin 92 into the recess 98 also results in the tripping of the tubing sensor 128.

Additionally, a segment of the tubing 88 extending between the pump fingers 52 and shut-off valve 14 rests upon one of the pressure sensor members 86, with a segment of the tubing 88 extending between the pump fingers 52 and the tubing locator pin 92 resting upon the other pressure sensor member 86. As also previously indicated, when the tubing assembly 12 is initially attached to the pump 10, the shut-off valve 14 thereof resides in its normal closed position, with the pinch arm 106 thereof being engaged to and completely collapsing the tubing 88.

Subsequent to the attachment of the tubing assembly 12 to the pump 10 in the above-described manner, the platen member 26 is moved from its non-operative position to its operative position as shown in FIG. 7. As indicated above, the movement of the platen member 26 to its operative position and engagement of the latch mechanism 30 thereof to the latch pins 32 results in the tripping of the platen sensor 120. When moved to its operative position, the inner surface 28 of the platen member 26 applies a slight amount of compressive pressure to that portion of the tubing 88 extending between the shut-off valve 14 and tubing locator pin 92. As such, the portion of the tubing 88 which is extended over the-row of pump fingers 52 is slightly compressed between the inner surface 28 of the platen member 26 and second ends 56 of the pump fingers 52, including the finger tips 82 of the pinch member 72 protruding therefrom. As a result, the pump fingers 52, and more particularly the roller members 58 disposed within the second ends 56 thereof, are biased against the cam 34.

Importantly, the platen member 26 is sized and configured to move the pinch arm 106 of the shut-off valve 14 from its normal closed position to its open position when the platen member 26 is moved to its operative position. In this respect, a portion of the platen member 26 acts against and applies pressure to the upper ends of the side bar portions 108 of the pinch arm 106, thus facilitating the compression of the biasing spring 114 and resultant movement of the pinch arm 106 to its open position. Additionally, the platen member 26 is pivotally connected to the support member 25 at a location whereat the movement of the platen member 26 from its non-operative position to its operative position results in the occlusion of the tubing 88 by at least one of the pinch members 72, and more particularly the finger tip 82 thereof, prior to the movement of the pinch arm 106 of the shut-off valve 14 from its closed position to its open position by the engagement of the platen member 26 thereagainst. As such, irrespective of whether the platen member 26 is in its operative or non-operative position, the tubing 88 is always occluded by either the shut-off valve 14 or one of the pinch members 72, thus effectively preventing any backflow of liquid therethrough.

Subsequent to the movement of the platen member 26 to its operative position, the pump 10 may be activated to facilitate the pumping of liquid through the tubing assembly 12 thereby. The ability to activate the pump 10 occurs as a result of both the tubing sensor 128 and platen sensor 120 being tripped by the interface of the tubing assembly 12 to the support member 25 and the closure of the platen member 26 (i.e., the movement of the platen member 26 to its operative position). As indicated above, since the platen and tubing sensors 120, 128 are electrically connected to each other in series, both must be tripped in order for the pump 10, and in particular the drive unit 36 thereof, to be activated.

In the pump 10, the cam 34 is configured to sequentially move the pump fingers 52 radially outwardly toward and inwardly away from the inner surface 28 of the platen member 26 when rotated in the first direction by the drive unit 36. In this respect, as the cam 34 rotates and acts against the roller members 58 within the first ends 54, the pump fingers 52 are sequentially extended and retracted in a wave-like fashion as observed from the perspective shown in FIG. 7, thus forcing liquid in the tubing 88 in the direction of rotation of the cam 34 (i.e., in a direction away from the end of the platen member 26 pivotally connected to the support member 25). As each successive pump finger 52 is fully radially extended outwardly and pressed against the tubing 88, the immediately preceding pump finger 52 begins to be withdrawn radially inwardly away from the tubing 88. When each pump finger 52 is moved to its position closest to the inner surface 28 of the platen member 26, the finger tip 82 of the pinch member 72 protruding from the second end 56 occludes the tubing 88. Thus, as indicated above, the rotation of the cam 34 forces liquid through the tubing 88 in the direction of cam rotation, with the occlusion of the tubing 88 which occurs as a result of the sequential action of the outwardly biased pinch members 72 thereagainst preventing any backflow of liquid within the tubing 88 when the platen member 26 is in its operative position, even upon the deactivation of the motor 42. As will be recognized, since the pumping of the liquid through the tubing 88 is dependent upon the sequential engagement of the second ends 56 of the pump fingers 52 thereagainst and the movement of the pump fingers 52 is dependent upon the rotation of the cam 34, the deactivation of the electric motor 42 which eliminates any rotation of the cam 34 due to the engagement between the worm 48 and the worm gear 40 assists in preventing any positive flow or backflow of liquid through the tubing 88.

Figure 15A:
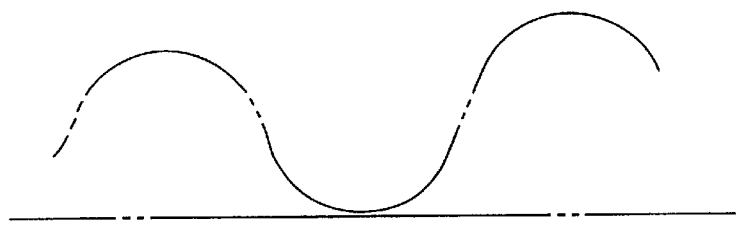
FIG. 15a is a graph illustrating a typical pump cycle of a prior art rotary peristaltic pump.
Figure 15B:
FIG. 15b is a graph illustrating a typical pump cycle of a prior art linear peristaltic pump.

In the pump 10, the sequential movement of the first through the last pump fingers 52 of the row toward and away from the platen member 26 by the rotation of the cam 34 defines a "pump cycle". During each "pump cycle", the engagement of the second ends 56 of the pump fingers 52 and pinch members 72 against the tubing 88 in the above-described manner forces liquid therethrough. As seen in FIG. 15a, in prior art rotary peristaltic pumps, the pump cycles are generated in a generally sinusoidal fashion, with each of the pump cycles being separated by a "dead pump phase" wherein no liquid is being forced through the tube of the pump. Additionally, during the pump cycle itself, the flow rate of liquid through the tube of the prior art rotary peristaltic pump is not constant, but rather undergoing almost continuous changes in velocity. As seen in FIG. 15b, in prior art linear peristaltic pumps, though a more constant rate of flow is achieved during each pump cycle, such pump cycles are separated by lengthy dead pump phases in which no liquid is being pumped through the tube of the prior art pump. As indicated above, it is significantly more desirable in a peristaltic pump for liquid to flow through the tube at a more uniform, steady rate with minimal changes in velocity or interruptions as are attributable to dead pump phases.

Figure 15C:
FIG. 15c is graph illustrating a typical pump cycle of the peristaltic pump of the present invention.

Referring now to FIG. 15c, in the pump 10, the cam 34 is profiled or shaped so as to act against the roller members 58 protruding from the first ends 54 of the pump fingers 52 in a manner causing the second ends 56 and pinch members 72 to engage the tubing 88 such that the flow rate of liquid therethrough is substantially constant throughout each pump cycle. Such constant flow rate is achieved by forming the cam 34 as a four lobe cam. In addition to the cam 34 being shaped to provide a substantially constant flow rate throughout each pump cycle, the motor speed control unit 60 of the pump 10 is operable to increase the rotational speed of the cam 34 in the first direction between pump cycles for purposes of substantially eliminating the dead pumping phase which normally exists between pump cycles. In this respect, the number and size of the encoder arms 70 of the encoder wheel 68 is selected such that interruptions in the beam of light L caused thereby correspond to the pump cycles, with the optical sensor 62 being operable to determine the beginning and end of each pump cycle and increase the power to the motor 42 and hence the rotational speed of the cam 34 between pump cycles which substantially reduces the dead pump phase. Typically, an additional four (4) volts of power is supplied to the motor 42 to achieve the desired level of increased rotational speed of the cam 34. The reduction in such dead pump phases, coupled with the more uniform flow rate occurring during each pump cycle as achieved by the profiling or shaping of the cam 34, provides a substantially uniform or constant rate of liquid flow through the tubing 88 of the tubing assembly 12 during the operation of the pump 10.

Figure 16:
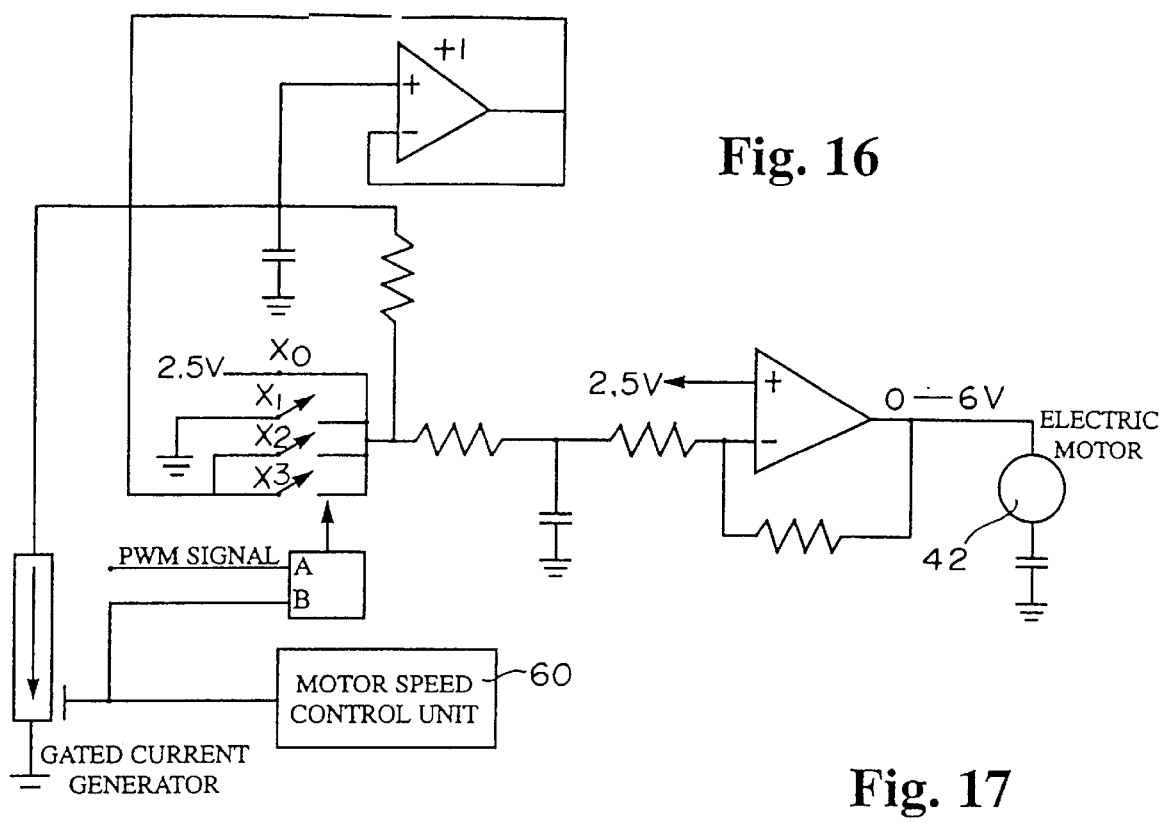
FIG. 16 is a schematic of the circuit used to facilitate the functional interface between the motor speed control unit of the present peristaltic pump and the drive unit thereof.

Referring now to FIG. 16, there is depicted an electrical schematic of the control circuit which functions as a closed loop feedback system and is used to :facilitate the operational interface between the motor speed control unit 60 and drive unit 36 of the present pump 10. A full schematic of the control circuit is included in the microfiche appendix to the present application and is incorporated herein by reference. As explained above, there is a dead zone portion of the pump cycle of the pump 10 where no pumping action occurs. Though this dead zone does not cause problems for higher infusion rates, it is highly undesirable in lower infusion rates. Accordingly, a speedup cycle has been implemented in the pump 10 to make its pump flow rate much more uniform by speeding up the pump rate during the dead zone portion of the pump cycle so that fluid flow is nearly constant, even at low flow rates.

In the pump 10, the speedup cycle is carefully tailored to minimize the acceleration command applied to the motor drive circuitry of the electric motor 42 in order to reduce the power spike caused by a sudden increase in the speed of the electric motor 42. In this respect, a simple low pass filter would not be adequate due to the large speed change rate involved in the pump 10. Since for a simple RC time constant the initial speed change is greatest, with the rate asymptotically approaching final value, a linear ramped response is required to facilitate a constant acceleration of the electric motor 42 and reduce motor current power spikes. More particularly, a speed-up signal is required which starts from an initial commanded rate, ramps up to a speed-up rate, and then returns to a programmed rate.

To mechanize the speedup cycle in the pump 10, the optical sensor 62 of the motor speed control unit 60 is used to generate a signal when speedup is required. In the circuit schematically shown in FIG. 16, the motor speedup signal generated by the optical sensor 62 is recovered and amplified to digital logic levels. The circuit also includes a gated temperature compensated current source and an integrated circuit which is a 4 to 1 analog multiplexer. The circuit generates a pulse width modulated (PWM) signal which enters the control input to the switch. During the "1" input, the switch is at ground. When the input is at "0", the switch is at a precision +2.5 volts. As such, the switch inverts the PWM signal and level converts it to a precision voltage for the proper input command to the driver of the electric motor 42. The input or motor speed command goes through a resistor and a capacitor, and is converted to a drive command. The same PWM signal is also sent through a resistor and a capacitor to recover the input command level to interact with the gated current generator. The circuit also includes a unity gain buffer amplifier to provide drive requirements for the switch. The speedup signal is at a much lower frequency than the 10 kHz PWM signal, and passes on to the electric motor 42 through a resistor when gated on.

During the operation of the pump 10, the pressure sensor members 86a and 86b generate electrical signals corresponding to the degree of expansion or compression, respectively, of the tubing 88 when acted upon by the pump fingers 52 and pinch members 72, thus providing warning of any over expansion and/or compression thereof. As indicated above, when the motor 42 is deactivated and the platen member 26 moved to its non-operative position, the shut-off valve 14 returns to its normal closed position and prevents any backflow of liquid through the tubing 88 in a direction opposite the first direction of rotation of the cam 34.

CONTROL SEQUENCE

Figure 17:
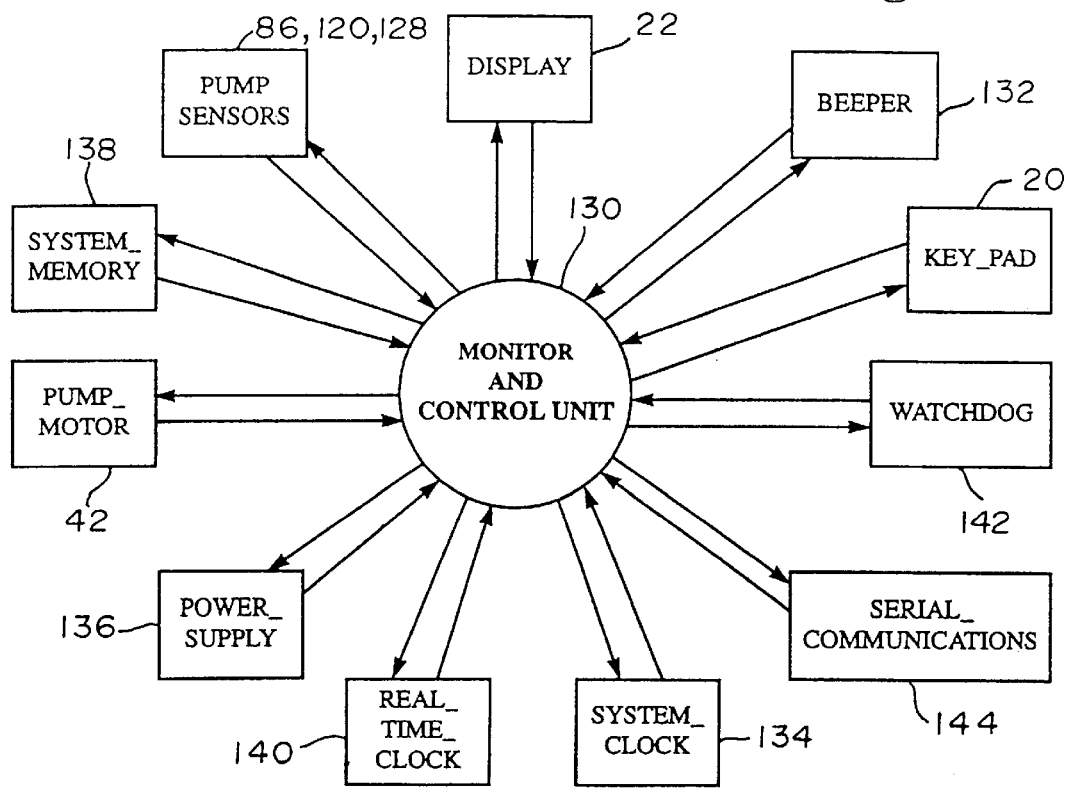
FIG. 17 is a flow chart illustrating the primary hardware and software interfaces of the present peristaltic pump.

Referring now to FIG. 17, the pump 10 of the present invention is provided with an internal monitor and control unit 130 which monitors, controls and coordinates the various operations thereof. The monitor and control unit 130 implements software of a specific design and architecture which imparts to the pump 10 various functional attributes not found in prior art peristaltic pumps.

As seen in FIG. 17, the monitor and control unit 130 is in electrical communication with a number of components of the pump 10, including the previously described key pad 20 which has an 19 key configuration. Included in the key pad 20 is an on/off key and a remote bolus button for the input of status and data to the software of the pump 10. Also in electrical communication with the monitor and control unit 130 is a beeper 132 of the pump 10 which is disposed within the interior of the housing 16. The beeper 132 contains two buzzers which operate at a single, fixed frequency. One of the buzzers, which is designated as the normal operation buzzer, is pulsed at varying widths, pulse rates and total number of pulses, as a function of the event to be signaled thereby. The second buzzer, which is designated as the auxiliary buzzer, operates from a watch dog time out. The second buzzer can be tested once and then reset via a clear auxiliary beeper input event.

Also in electrical communication with the monitor and control unit 130 is a system clock 134 and the previously described display 22. The system clock 134 is a processor timer interrupt which is set at approximately 53.3 milliseconds. The display 22 preferably consists of a 100×32 dot graphical LCD display and three individual LED's which are located on the key pad 20. The LCD display is used to provide data information to the user, with the LED's being used to provide status information to the user.

In addition to the above-described components, various pump sensors are in electrical communication with the monitor and control unit 130, including the above-described pressure sensor members 86, platen sensor 120, and tubing sensor 128. In addition to these particular sensors, the pump 10 may also be provided with air in-line sensors at the beginning and end of that portion of the tubing 88 extending over the membrane 126, and peristaltic cam drive sensors which monitor the revolution or rotation of the cam 34. The electric motor 42 of the drive unit 36 is also in electrical communication with the monitor and control unit 130, as is a power supply 136 of the pump 10. As previously explained, the electric motor 42 facilitates the rotation of the cam 34, and hence drives the pump 10. As also previously explained, the power supply 136 may comprise one or more batteries which are stored within the interior of the housing 16, such as a 3-volt battery or a lithium battery. Alternatively, the power supply 136 may comprise a 3-volt external power source which is electrically connected to the housing 16 and placed into electrical communication with the necessary components of the pump 10.

In addition to the foregoing, also in electrical communication with the monitor and control unit 130 is a system memory 138, a real time clock 140, a watch dog 142, and a serial communications port 144. The real time clock 140 provides a reference for the date and time of day, with this information being read therefrom on demand. The serial communications port 144 is preferably an asynchronous serial port, 9600 bps full duplex, with no RTS or CTS, RDX and TXD only. The watch dog 142 is an independent, re-triggered one shot which is attached to a microcontroller NMI input and a motor inhibit control input of the pump 10. The watch dog 142 must be "petted", at least once per 1.6 seconds, and also provides a test capability which can be activated to cause the watch dog 142 to time out but not reset the microcontroller of the pump 10 one time after the power-up thereof.

The monitor and control unit 130 of the pump 10 controls the infusion process and monitors the process to prevent over infusion. The monitor and control unit 130 also provides for the user selection and programming of five different therapies, including:

1. Continuous infusion—designed to allow a constant programmed rate of infusion;
2. PCA or Patient Controlled Analgesia—designed for therapies that require a continuous rate of infusion, patient controlled demand boluses, or both;
3. TPN with Automatic Ramping—designed to allow a level rate of infusion of parenteral nutritional products with the option of tapering at the beginning, end or both of the infusion, and having an early ramp-down feature;
4. Intermittent Delivery—designed to deliver programmed intervals and rates of specified amounts of infusates and to optionally deliver small amounts of the infusion between doses to keep the patient's access site patent; and
5. Variable Program—designed to allow varying amounts, rates and times of delivery of infusions up to twenty four (24) specified programs.

As such, the pump 10 can be used for intravenous, intra-arterial, epidural, subcutaneous, or enteral therapies. The pump 10 can also be used to deliver medications from a medication reservoir, from IV bags, or from syringes.

Upon the start-up of the pump 10, a "validate pump process" implemented by the software initiates the operation of the monitor and control unit 130, and more particularly the software thereof. The validate pump process performs a number of functions, including a "boot" which is entered from power-up reset and initializes the monitor and control unit 130 and the input/outputs thereof to the proper configuration. The boot performs a test on the boot code and start-up code of the software to verify their validity, and also is able to accept a special command to download code to a flash ROM. The boot also verifies that a valid program is downloaded into the flash ROM before operation of the pump 10 is permitted to proceed. The boot will also first verify via a CRC algorithm that the boot code is good.

In addition to the boot, the validate pump process performs a "start-up" which verifies that the pump 10, including both its hardware and software, is functioning properly by performing the required start tests on the monitor and control unit 130, system memory 138, pump monitor sensors 86, 120, 124, drive unit 36, and all aspects of the hardware of the pump 10. If these tests pass, control will transfer to a "program select" function of the validate pump process, otherwise it will transfer to a malfunction phase.

The program select function of the validate pump process provides a means to the user for selecting normal pump operation (transfer to programming), or allowing the user to perform special set-up functions. Access to such special set-up functions requires a special access code by the user, with such set-up transferring directly to the normal operation of the pump 10. These special set-up functions include printing the history files and other pertinent data of a patient. A further function of the validate pump process is "factory calibration" which provides for the calibration of the pump 10. These functions are also accessed only by a special access code, and are manually commanded.

The software of the monitor and control unit 130 also implements a "create therapy process" which accepts inputs from the user for programming up to five (5) different infusion therapies. Such programming includes the selection of the therapy to be programmed, the programming of the pump 10 and therapy options, and the programming of the prescription for the infusion. A therapy may be programmed as a new therapy, a repeat of an existing therapy, changes in an existing therapy, or continue with a therapy in process which was previously interrupted. After a therapy has been validated by requiring the user to select each prescription parameter with the push of the yes key of the key pad 20, execution will transfer to a notification menu to allow the start of the infusion.

The pump 10 of the present invention includes numerous other operational attributes which are implemented by various aspects of its hardware and software. A comprehensive treatment of this functionality and the hardware and software which implements the same is set forth in the documents which are included in microfiche appendix of the present application and are incorporated herein by reference.

Additional modifications and improvements of the present invention may also be apparent to those of ordinary skill in the art. Thus, the particular combination of parts described and illustrated herein is intended to represent only one embodiment of the present invention, and is not intended to serve as limitations of alternative devices within the spirit and scope of the invention.

What is claimed is:

1. An administration set for use with a curvilinear peristaltic pump, the administration set comprising:

a length of straight line, resilient tubing;

at least one tubing sensor disposed in a housing of the pump; and first and second locating members removably insertable into the housing of the pump and positionable upon the tubing at locations whereat the insertion of the locating members into the pump ensure that a portion of the tubing is in contact with the pump, the first locating member is engageable with the tubing sensor to communicate proper insertion of the locating member to the pump.

2. The administration set of claim 1 wherein the first locating member is a tubing locator pin attached to the tubing; and the second locating member is a flow stop member attached to the tubing and operative to selectively obstruct the flow of liquid therethrough.

3. The administration set of claim 1 wherein the tubing is fabricated as a continuous polyvinyl chloride member.

* * * * *